US012564718B2

(12) United States Patent
Mukesh et al.

(10) Patent No.: US 12,564,718 B2
(45) Date of Patent: Mar. 3, 2026

(54) MAGNETIC ELECTRODE COCHLEAR IMPLANT WITH IN-SITU STIMULATION ADJUSTMENTS

(71) Applicant: INTERNATIONAL BUSINESS MACHINES CORPORATION, Armonk, NY (US)

(72) Inventors: Sagarika Mukesh, Albany, NY (US); John S. Werner, Fishkill, NY (US); Arkadiy O. Tsfasman, Wappingers Falls, NY (US); Steven Holmes, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 945 days.

(21) Appl. No.: 17/805,033

(22) Filed: Jun. 2, 2022

(65) Prior Publication Data

US 2023/0390559 A1 Dec. 7, 2023

(51) Int. Cl.
*A61N 1/36* (2006.01)
*A61N 1/05* (2006.01)

(52) U.S. Cl.
CPC ....... *A61N 1/36139* (2013.01); *A61N 1/0541* (2013.01); *A61N 1/36038* (2017.08)

(58) Field of Classification Search
CPC .............. A61N 1/0541; A61N 1/36038; A61N 1/36039; A61N 1/36139
See application file for complete search history.

(56) References Cited

U.S. PATENT DOCUMENTS

| 5,344,387 | A | 9/1994 | Lupin | |
|---|---|---|---|---|
| 6,810,289 | B1 | 10/2004 | Shaquer | |
| 9,744,358 | B2 | 8/2017 | Hehrmann | |
| 2005/0261748 | A1* | 11/2005 | van Dijk | A61N 1/36039 607/57 |

(Continued)

FOREIGN PATENT DOCUMENTS

EP        3142388 A1      3/2017

OTHER PUBLICATIONS

Mell et al., "The NIST Definition of Cloud Computing", National Institute of Standards and Technology, Special Publication 800-145, Sep. 2011, 7 pages.

(Continued)

*Primary Examiner* — Amanda K Hulbert
(74) *Attorney, Agent, or Firm* — Anthony M. Pallone

(57) ABSTRACT

According to one embodiment, a method, computer system, and computer program product for performing in-situ stimulation adjustments of a cochlear implant. The embodiment may include identifying, dynamically, a first set of magnetic coils and a second set of magnetic coils based on dominant frequency components of a received sound. The first set and the second set are implanted within a cochlea of a user having a cochlear implant (CI). The embodiment may include activating, according to a stimulator profile of the user, the first set via an electric current sent to the first set in order to stimulate cochlear neurons. The embodiment may include determining that an in-situ adjustment to the activation of the first set is required based on analysis of a cochlear neuronal response recorded via the second set. The embodiment may include adjusting the stimulator profile.

20 Claims, 5 Drawing Sheets

(56) References Cited

U.S. PATENT DOCUMENTS

| 2008/0249589 | A1 | 10/2008 | Cornejo Cruz | |
| 2015/0018699 | A1 | 1/2015 | Zeng | |
| 2016/0213943 | A1* | 7/2016 | Mauger | A61N 2/006 |
| 2020/0030605 | A1 | 1/2020 | Kals | |

OTHER PUBLICATIONS

Mukesh et al., "Magnetic Stimulation of Dissociated Cortical Neurons on a Planar Mulitelectrode Array*," IEEE, 9th International IEEE EMBS Conference on Neural Engineering, San Francisco, CA, USA, Mar. 20-23, 2019, pp. 758-761.
Mukesh, et al., "Modeling Intracochlear Magnetic Stimulation: A Finite-Element Analysis," IEEE Transactions on Neural Systems and Rehabilitation Engineering, vol. 25, No. 8, Aug. 2017, pp. 1353-1362.

* cited by examiner

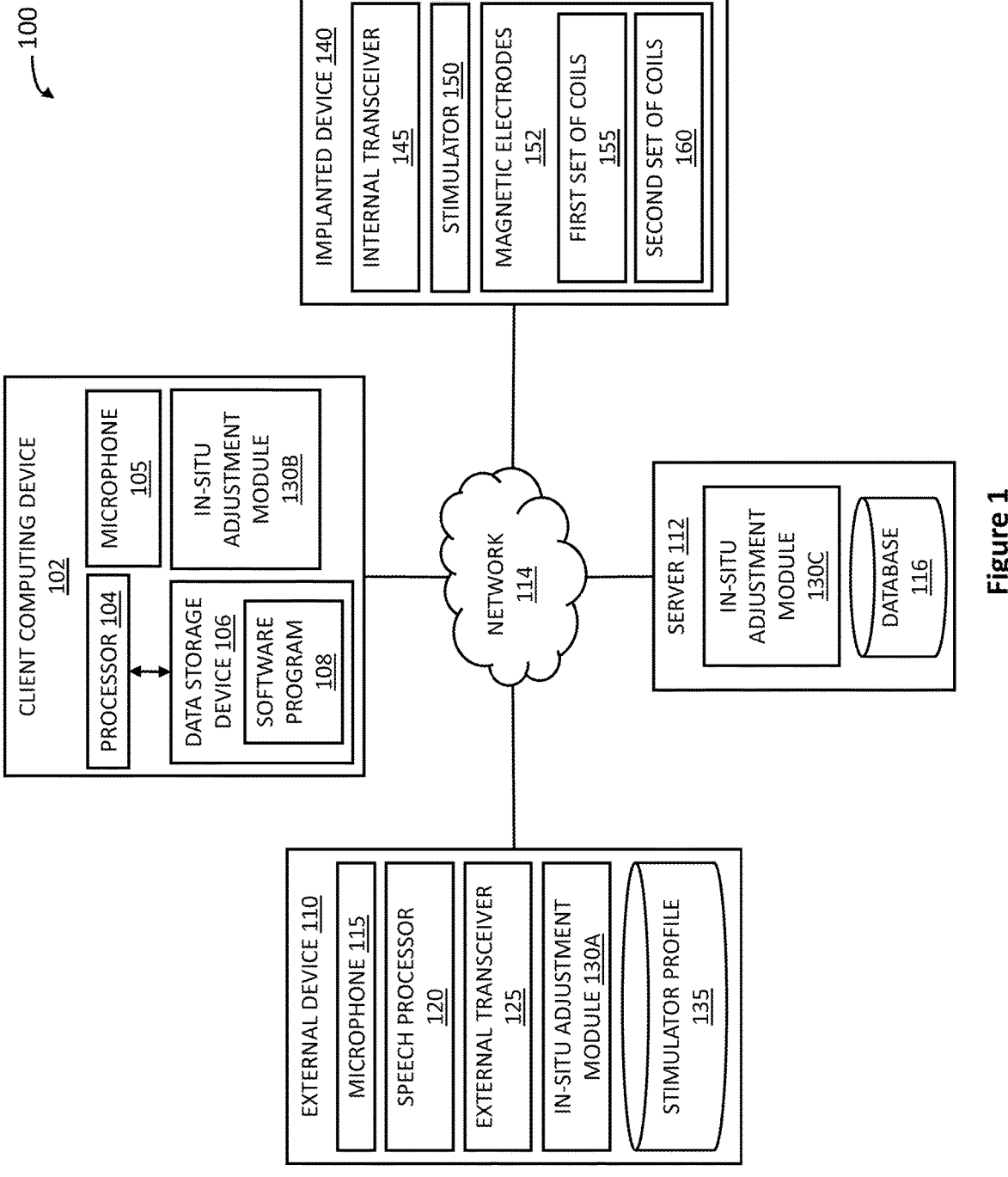

100

IMPLANTED DEVICE 140
INTERNAL TRANSCEIVER 145
STIMULATOR 150
MAGNETIC ELECTRODES 152
FIRST SET OF COILS 155
SECOND SET OF COILS 160

CLIENT COMPUTING DEVICE 102
MICROPHONE 105
IN-SITU ADJUSTMENT MODULE 130B
PROCESSOR 104
DATA STORAGE DEVICE 106
SOFTWARE PROGRAM 108

NETWORK 114

SERVER 112
IN-SITU ADJUSTMENT MODULE 130C
DATABASE 116

EXTERNAL DEVICE 110
MICROPHONE 115
SPEECH PROCESSOR 120
EXTERNAL TRANSCEIVER 125
IN-SITU ADJUSTMENT MODULE 130A
STIMULATOR PROFILE 135

Figure 1

MAGNETIC ELECTRODE COCHLEAR IMPLANT WITH IN-SITU STIMULATION ADJUSTMENTS

BACKGROUND

The present invention relates generally to the field of computing, and more particularly to cochlear implants.

A cochlear implant (CI) is a surgically implanted small electronic device that provides a person having moderate to profound sensorineural hearing loss with sound perception. A CI has two main components; an outside (i.e., external) component, which is generally worn behind the ear, and an inside (i.e., implanted) component. The outside component typically includes one or more microphones which capture sound from an environment of the person, a speech processor which selects, and processes sounds captured by the microphone(s), and a transmitter that sends power and the processed sound signals across the skin to the inside component via radio frequency transmission. The inside component typically includes a receiver/stimulator, which receives signals from the speech processor and converts them into electric impulses, and an electrode array embedded within the person's cochlea which collects the electric impulses from the stimulator and sends them to different regions of the cochlear nerve. Therefore, a CI bypasses acoustic hearing by direct electrical stimulation of the cochlear nerve.

SUMMARY

According to one embodiment, a method, computer system, and computer program product for performing in-situ stimulation adjustments of a cochlear implant. The embodiment may include identifying, dynamically, a first set of magnetic coils and a second set of magnetic coils based on dominant frequency components of a received sound. The first set and the second set are implanted within a cochlea of a user having a cochlear implant (CI). The embodiment may include activating, according to a stimulator profile of the user, the first set via an electric current sent to the first set in order to stimulate cochlear neurons. The embodiment may include determining that an in-situ adjustment to the activation of the first set is required based on analysis of a cochlear neuronal response recorded via the second set. The embodiment may include adjusting the stimulator profile.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings:

FIG. 1 illustrates an exemplary networked computer environment according to at least one embodiment.

DETAILED DESCRIPTION

Figure 2:
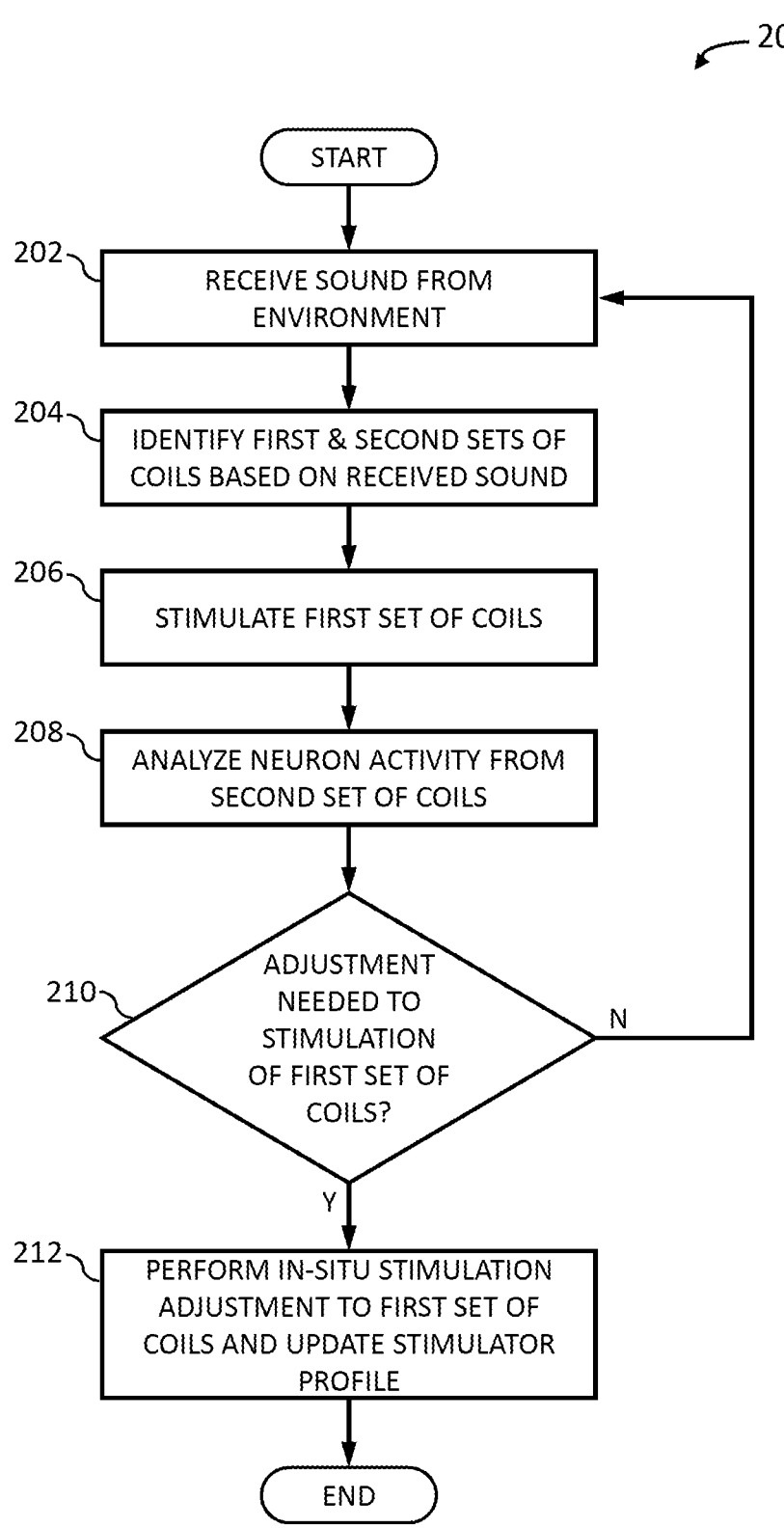
FIG. 2 illustrates an operational flowchart for providing in-situ stimulation adjustments of a CI with magnetic electrodes in an in-situ stimulation adjustment process according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

It is to be understood that the singular forms "a," "an," and "the" include plural referents unless the context clearly dictates otherwise. Thus, for example, reference to "a component surface" includes reference to one or more of such surfaces unless the context clearly dictates otherwise.

Embodiments of the present invention relate generally to the field of computing, and more particularly to cochlear implants with magnetic electrodes. The following described exemplary embodiments provide a system, method, and program product to, among other things, provide in-situ stimulation adjustments of a cochlear implant with magnetic electrodes. Therefore, the present embodiment has the capacity to improve the technical field of cochlear implants with magnetic electrodes by dynamically adjusting, in-situ, an electric current sent to one or more magnetic coils, implanted within the cochlea of a user, which are used to stimulate cochlear neurons.

As previously described, a CI is a surgically implanted small electronic device that provides a person having moderate to profound sensorineural hearing loss with sound perception. A CI has two main components; an outside (i.e., external) component, which is generally worn behind the ear, and an inside (i.e., implanted) component. The outside component typically includes one or more microphones which capture sound from an environment of the person, a speech processor which selects, and processes sounds captured by the microphone(s), and a transmitter that sends power and the processed sound signals across the skin to the inside component via radio frequency transmission. The inside component typically includes a receiver/stimulator, which receives signals from the speech processor and converts them into electric impulses, and an electrode array embedded within the person's cochlea which collects the electric impulses from the stimulator and sends them to different regions of the cochlear nerve. Therefore, a CI bypasses acoustic hearing by direct electrical stimulation of the cochlear nerve.

Research has demonstrated that stimulating the cochlear nerve using an induced electric field produced by a time varying magnetic field provides enhanced cochlear neuron stimulation capabilities in CIs with a magnetic electrode array embedded within a user's cochlea. In such CIs (i.e., magnetic coil CIs), different magnetic coils within the electrode array of the implant are activated dependent upon the dominant frequencies of the incoming sound signals from the speech processor. However, many times the electric current sent to a magnetic coil may not be correct or sufficient for generating a desired neuronal response within the cochlear nerve; indicating that the user of the CI will not receive the expected hearing sensation for the given sound.

Such an outcome may not only lead to poor performance of the CI, but also to wasted power and decreased battery life of the CI when electric current is sent to one or more magnetic coils which are not providing a hearing benefit to the user. While programming/tuning adjustments may be made to the CI, such adjustments are typically made by an Audiologist which the user may typically see once or twice a year for recalibration of the CI. It may therefore be imperative to have a system in place to perform, with increased frequency, in-situ stimulation adjustments to a user's CI having magnetic electrodes. Thus, embodiments of the present invention may be advantageous to, among other things, improve performance and increase battery life of a CI with magnetic electrodes. The present invention does not require that all advantages need to be incorporated into every embodiment of the invention.

According to at least one embodiment, a sound may be captured by a user's CI having magnetic electrodes which include a set of coils. The dominant frequencies of the sound may be identified, and the set of coils may be divided into a first and a second set of coils based on the dominant frequencies of the sound. An electric current may be sent to the first set of coils in order to stimulate desired cochlear neurons, concurrently, the second set of coils is used to monitor neuronal activity of the cochlear neurons. The electric current sent to the first set of coils may be increased or decreased based on analysis of the monitored neuronal activity. According to at least one other embodiment, one or more coils of the first set of coils may be permanently assigned to the second set of coils, and consequently not send future electric current, based on analysis of the monitored neuronal activity.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed concurrently or substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product to identify a first and a second set of magnetic coils of a CI based on captured dominate sound frequencies and, accordingly, adjust an electric current sent to the first set of magnetic coils based on neuronal activity measured by the second set of magnetic coils.

Referring to FIG. 1, an exemplary networked computer environment 100 is depicted, according to at least one embodiment. The networked computer environment 100 may include a client computing device 102, a server 112, an external device 110, and an implanted device 140 interconnected via a communication network 114. According to at least one implementation, the networked computer environment 100 may include a plurality of client computing devices 102 and servers 112, of which only one of each is shown for illustrative brevity. Additionally, in one or more embodiments, the external device 110, the client computing device 102, and the server 112 may each individually host an in-situ adjustment (ISA) module 130A, 130B, 130C, respectively. In one or more other embodiments, the ISA module 130A, 130B, 130C may be partially hosted on external device 110, client computing device 102, and server 112 so that functionality may be separated among the devices.

The communication network 114 may include various types of communication networks, such as a personal area network (PAN), wide area network (WAN), local area network (LAN), a telecommunication network, a wireless network, a wireless ad hoc network (i.e., a wireless mesh network), a public switched network, a radio frequency (RF) network, an inter-integrated circuit (I2C) serial communication bus, the Serial Peripheral Interface (SPI), a universal asynchronous receiver-transmitter (UART), and/or a satellite network. The communication network 114 may include connections, such as wired or wireless communication links or fiber optic cables. It may be appreciated that FIG. 1 provides only an illustration of one implementation and does not imply any limitations with regard to the environments in which different embodiments may be implemented. Many modifications to the depicted environments may be made based on design and implementation requirements. In one or more embodiments, there may be multiple networks 114 within the exemplary networked computer environment 100 each supporting a different communication protocol among the client computing device 102, the server 112, the external device 110, and the implanted device 140. For example, a first network 114 may include a RF network supporting communications between the external device 110 and the implanted device 140, a second network 114 may include a wireless Bluetooth® network (Bluetooth and all Bluetooth-based trademarks and logos are trademarks or registered trademarks of Bluetooth SIG, Inc. and/or its affiliates) supporting communications between the external device 110 and the client computing device 102, and a third network 114 may include a wireless network (e.g., Wi-Fi) supporting communications between the client computing device 102 and the server 112.

Client computing device 102 may include a processor 104 and a data storage device 106 that is enabled to host and run a software program 108 and an ISA module 130B and communicate with the external device 110 and the server 112 via the communication network 114, in accordance with embodiments of the invention. Client computing device 102 may also include a microphone 105 capable of capturing sound within an environment. Client computing device 102 may be, for example, a mobile device, a smartphone, a personal digital assistant, a netbook, a laptop computer, a tablet computer, a desktop computer, or any type of computing device capable of running a program and accessing a network. As will be discussed with reference to FIG. 3, the client computing device 102 may include internal components 402b and external components 404b, respectively.

The server computer 112 may be a laptop computer, netbook computer, personal computer (PC), a desktop computer, or any programmable electronic device or any network of programmable electronic devices capable of hosting and running an ISA module 130C and a database 116 and communicating with the client computing device 102 and the external device 110 via the communication network 114, in accordance with embodiments of the invention. As will be discussed with reference to FIG. 3, the server computer 112 may include internal components 402c and external components 404c, respectively. The server 112 may also operate in a cloud computing service model, such as Software as a Service (SaaS), Platform as a Service (PaaS), or Infrastructure as a Service (IaaS). The server 112 may also be located in a cloud computing deployment model, such as a private cloud, community cloud, public cloud, or hybrid cloud.

External device 110 may include a microphone 115, a speech processor 120, and an external transceiver 125, and may be enabled to host and run a stimulator profile 135 and an ISA module 130A and communicate with the implanted device 140 and the server 112 via the communication network 114, in accordance with embodiments of the invention. The microphone 115 may be capable of capturing sound within an environment of a user. Although only one microphone 115 is depicted in FIG. 1, in another embodiment the external device 110 may include multiple microphones 115. The speech processor 120 may be capable of receiving sound input from the microphone 115, performing a Fourier transform on the received sound input to identify its dominant frequency components, accessing the stimulator profile 135, and sending its output to the external transceiver 125. The external transceiver 125 may be capable of receiving output from the speech processor 120 and sending that output to the internal transceiver 145 via RF signals. The stimulator profile 135 may be a database storing a tonotopic mapping of a user's cochlea which correlates different frequency input regions of the user's cochlea, from its base to its apex, with one or more identified coils of the magnetic electrodes 152 (discussed below) to be activated. Additionally, for each identified coil of the magnetic electrodes 152, the stimulator profile 135 may also store an identified electric current value required to activate the coil based on a volume of its corresponding frequency input. Although the stimulator profile 135 is depicted as being stored within the external device 110, in at least one other embodiment the stimulator profile 135 may be additionally stored within the data storage device 106 or the database 116, or both. In embodiments of the invention, the external device 110 may be any known computing device of a CI which is located external to the user's skull and capable of communicating with a corresponding implanted device of the CI. As will be discussed with reference to FIG. 3, the external device 110 may include internal components 402a and external components 404a, respectively.

According to at least one embodiment, the speech processor 120 may also receive sound input from the microphone 105 located on the client computing device 102 via the network 114 provided the client computing device 102 is within a threshold distance from the external device 110. For example, a microphone of the user's smartphone, which is located near the user, may capture sound input from the user's environment which may be processed by the speech processor 120 of the external device 110.

Implanted device 140 may include an internal transceiver 145, a stimulator 150, and magnetic electrodes 152, and may communicate with the external device 110 via the communication network 114, in accordance with embodiments of the invention. The internal transceiver 145 may be implanted under the skin behind the ear of the user and capable of receiving output of the speech processor 120, via one or more RF signals from the external transceiver 125, and sending received RF signals to the stimulator 150. The magnetic electrodes 152 may include a set of micro-scale magnetic coils which are placed within the user's cochlea and used to stimulate cochlear neurons such that the user may interpret sound within their environment. The magnetic coils of the set may be dynamically assigned to a first set of coils 155 or a second set of coils 160 based on the sound input captured by the microphone 115. The stimulator 150 may receive one or more RF signals (containing output from speech processor 120) and send an electric current to (i.e., activate) magnetic coils of the first set of coils 155. In embodiments of the invention, the implanted device 140 may be any known internal component of a CI which is implanted under the skin behind the ear and within the cochlea of the user and capable of communicating with a corresponding external device of the CI.

According to the present embodiment, the ISA module 130A, 130B, 130C may be a program capable of dynamically assigning magnetic coils of a magnetic electrode array of a CI to a first set of coils or a second set of coils based on their proximity to received dominant sound frequencies of an environment, accessing a CI stimulator profile of a user, sending an electric current to the magnetic coils of the first set of coils to stimulate desired neurons such that sound information may be sent to the user's brain to produce a hearing sensation, analyzing/recording neuronal activity via the magnetic coils of the second set of coils, adjusting, in-situ, the electric current sent to the magnetic coils of the first set of coils based on analyzed neuronal activity, and, accordingly, dynamically updating the CI stimulator profile of the user. In at least one embodiment, the ISA module 130A, 130B, 130C may require a user to opt-in to system usage upon opening or installation of the ISA module 130A, 130B, 130C. The ISA method is explained in further detail below with respect to FIG. 2.

Referring now to FIG. 2, an operational flowchart for providing in-situ stimulation adjustments of a CI with magnetic electrodes in an in-situ stimulation adjustment process 200 is depicted according to at least one embodiment. At 202, the ISA module 130A, 130B, 130C receives a sound input from a user's environment. The received sound input may have been captured by a microphone (e.g., microphone 115) of the CI which is recording incoming sound from the environment. Additionally, the ISA module 130A, 130B, 130C may, via the speech processor 120, perform a Fourier transform on the received sound input in order to identify its dominant frequency components.

Next, at 204, the ISA module 130A, 130B, 130C identifies a first set and a second set of magnetic coils of the CI having magnetic electrodes (e.g., magnetic electrodes 152) placed within the user's cochlea. The magnetic electrodes may include a set of individually identified micro-scale magnetic coils from which the ISA module 130A, 130B, 130C may assign coils of the set to a first set of coils (e.g., first set of coils 155) or a second set of coils (e.g., second set of coils 160). In making these identifications/assignments, the ISA module 130A, 130B, 130C may reference a stimulator profile (e.g., the stimulator profile 135) of the user. As noted above, the stimulator profile 135 may store a tonotopic mapping of the user's cochlea which identifies different frequency input regions within the cochlea which typically ranges from 20,000 Hz at its base to 20 Hz at its apex. This mapping may correlate the different frequency input regions of the user's cochlea with one or more of the individually identified coils of the magnetic electrodes 152 based on their placement proximities to the different frequency input regions within the user's cochlea. The stimulator profile 135 may specify which individually identified coils of the magnetic electrodes 152 to identify as being within (i.e., assign to) the first set of coils 155 based on the dominant frequency components of the received sound input. Additionally, for each identified coil of the magnetic electrodes 152, the stimulator profile 135 may also store a specified electric current value with which to activate the coil. The ISA module 130A, 130B, 130C may assign an identified magnetic coil of the magnetic electrodes 152 to the first set of coils 155 or the second set of coils 160 based on its proximity/correlation to the dominant frequency components of the received sound input identified at 202.

According to at least one embodiment, the stimulator profile 135 may store multiple electric current values for specified frequencies, or specified frequency ranges, to account for different volume levels of the received sound input. Frequency-to-current correlations may be represented via a curve for each frequency, or frequency range, on a volume vs. current graph having electric current values and volume levels on the X and Y axis, respectively. The volume vs. current graph may be stored within the stimulator profile 135 and accessed by the ISA module 130A, 130B, 130C. According to at least one further embodiment, the stimulator profile 135 may also store a multiplication factor for each specified frequency or specified frequency range. A received sound input may be converted to a generic/default electric current value based on an actual volume level of the received sound input, and the ISA module 130A, 130B, 130C may utilize the multiplication factor stored for the frequency of the received sound input to adjust the electric current sent to the first set of coils 155.

For example, if there are a total of 20 magnetic coils placed between the base and the apex of the user's cochlea and the dominant frequency components of the received sound input ranges between 900 Hz and 2000 Hz, identified coils 6, 7, and 8, whose placement proximity within the user's cochlea correlates to the input range of 900 Hz to 2000 Hz, may be assigned to the first set of coils 155. The remaining 17 magnetic coils may be assigned to the second set of coils 160. As another example, if there are a total of 20 magnetic coils placed between the base and the apex of the user's cochlea and the dominant frequency components of the received sound input ranges between 5000 Hz and 9000 Hz, identified coils 12, 13, 14, and 15, whose placement proximity within the user's cochlea correlates to the input range of 5000 Hz and 9000 Hz, may be assigned to the first set of coils 155. The remaining 16 magnetic coils may be assigned to the second set of coils 160. As illustrated in both examples, identified coils of the magnetic electrodes 152 which are not assigned to the first set of coils 155 are automatically assigned to the second set of coils 160.

According to at least one embodiment, an initial configuration of the stimulator profile 135 may be performed by a medical provider (e.g., an audiologist) of the user. The initial configuration may include identifying an initial tonotopic map of the user, defining initial correlations between the different frequency input regions of the user's cochlea and the individually identified coils of the magnetic electrodes 152 based on their placement proximities to the different frequency input regions within the user's cochlea, and defining, for each identified coil, an initial electric current value or multiplication factor with which to activate the coil based on the volume of the received sound input. The stimulator profile 135 may also be configured to store coil set assignment designations (i.e., first set of coils 155 or second set of coils 160) for identified coils. Moreover, the stimulator profile 135 may also store assignment designations for identified coils which are to be permanently assigned to the second set of coils 160. Upon initial configuration of the stimulator profile 135, none of the identified coils may be designated for permanent assignment to the second set of coils 160. The frequency correlation, the electric current activation value, and the assignment designation of an identified coil may be referred to as attributes of an identified coil.

At 206, the ISA module 130A, 130B, 130C stimulates the identified magnetic coils which are assigned to the first set of coils 155 by sending, via the stimulator 150, an electric current (e.g., a measure of microamps or milliamps) to the first set of coils 155. The value of the sent electric current may be the electric current value or a multiplication factor to the signal amplitude based on sound volume specified in the stimulator profile 135 for the identified magnetic coils of the first set of coils 155 and referenced in 204. The sent electric current may activate the identified magnetic coils of the first set of coils 155 which in turn may stimulate the desired cochlear neurons such that sound information may be sent to the user's brain to produce a hearing sensation and allow the user to interpret sound within their environment. The desired cochlear neurons may be those neurons within the user's cochlea which are in proximity to the frequency input regions that correlate to the dominant frequency components of the received sound input identified at 202. The desired cochlear neurons may produce neuronal activity in the form of action potentials upon stimulation.

Next, at 208, the ISA module 130A, 130B, 130C analyzes neuronal activity of the desired cochlear neurons utilizing the second set of coils 160. As noted above, any identified magnetic coils of the magnetic electrodes 152 which are not utilized for stimulation (i.e., are not assigned to the first set of coils 155) may be automatically assigned to the second set of coils 160 to record any neuronal activity occurring within their placement proximities. The second set of coils 160 may act as antennas to measure/capture neuronal response (i.e., electric current indued by action potentials) within the user's cochlea and send their captured signals to the ISA module 130A, 130B, 130C. As the magnetic coils used for stimulation (i.e., the first set of coils 155) and the magnetic coils used for neuronal response recording (i.e., the second set of coils 160) are inductor like coils, any time-varying magnetic fields, including those resulting from an action potential, may induce electric current within the second set of coils 160 which may be captured and sent to the ISA module 130A, 130B, 130C using internal transceiver 145, network 114, and external transceiver 125. According to the Ampere-Maxwell law, the second set of coils 160 will be perturbed by the electrical activity nearby. Using a simple threshold filter, noise due to stimulation (a common artifact) may be eliminated and spike sorting may be used to identify any action potentials. Presence of an action potential signifies cochlear neuronal activity, whereas a lack of action potentials signifies a lack of active cochlear neurons in the vicinity. In one or more embodiments, the impact of magnetic fields generated by the magnetic coils of the first set of coils 155 on the magnetic coils of the second set of coils 160 may be known and accounted for when analyzing neuronal response. It should be noted that no electric power from the stimulator 150 is required for the second set of coils 160. It should also be noted that in current magnetic cochlear implants, the second set of coils as described herein is not used since they are not stimulated for the current sound within the environment.

At 210, the ISA module 130A, 130B, 130C determines whether adjustment is needed to the stimulation of the first set of coils 155. This determination may be based on the cochlear neuronal response analyzed at 208 (i.e., the presence or lack of action potentials). Activation of the first set of coils 155 which in turn does not result in the stimulation of the desired cochlear neurons, or if neural response measured by the second set of coils 160 is below a threshold, may indicate that an adjustment to the stimulation/activation of the first set of coils 155 is required. In response to determining that the desired cochlear neurons have been stimulated (i.e., action potentials were present) and that stimulation adjustment to the first set of coils 155 is not required (step 210, "N" branch), the in-situ stimulation adjustment process 200 may return to step 202 to receive any future incoming sounds from the user's environment. In response to determining that the desired cochlear neurons have not been stimulated or if stimulation is below a threshold (i.e., action potentials were low or not present) and that stimulation adjustment to the first set of coils 155 is required (step 210, "Y" branch), the in-situ stimulation adjustment process 200 may proceed to step 212.

Next at 212, the ISA module 130A, 130B, 130C dynamically adjusts, in-situ, the stimulation of the first set of coils 155. More specifically, the ISA module 130A, 130B, 130C may adjust the electric current sent, via the stimulator 150, to the first set of coils 155. As the sent electric current is adjusted, the ISA module 130A, 130B, 130C may also, accordingly, dynamically adjust, in-situ, the stimulator profile 135 of the user to reflect changes to the specified electric current values with which to activate the identified magnetic coils of the first set of coils 155. According to at least one embodiment, the ISA module 130A, 130B, 130C may first increase the electric current sent to one or more identified magnetic coils of the first set of coils 155. The sent electric current may be increased in intervals up to a maximum permittable electric current value. The stimulator profile 135 may also be updated in-situ with the increased electric current values with which to activate the one or more identified magnetic coils. After in-situ adjustment has been made to the stimulation of the first set of coils 155, and consequently to the stimulator profile 135, the in-situ stimulation adjustment process 200 may end or return to step 202.

According to at least one other embodiment, in a scenario in which the electric current sent to one or more identified magnetic coils of the first set of coils 155 has been increased to the maximum permitted value however little (e.g., below a threshold value) or no neuronal activity of the desired cochlear neurons is recorded via the second set of coils 160, the ISA module 130A, 130B, 130C may update the stimulator profile 135 in-situ to permanently assign one or more magnetic coils of the first set of coils 155 to the second set of coils 160. Such a scenario may indicate that the cochlear neurons in proximity to one or more identified magnetic coils of the first set of coils 155 are no longer active (e.g., those cochlear neurons may be dead). As such, the user may not receive a benefit (i.e., a hearing sensation) by future activation of those one or more identified magnetic coils. As a result of not sending, via the stimulator 150, future electric current to the identified one or more magnetic coils permanently assigned to the second set of coils 160, the ISA module 130A, 130B, 130C may improve functionality and extend the battery life of the CI. As an illustration, consider that a single magnetic coil draws approximately 250 milliwatts (mW) of power if it is constantly on. For the following illustration, assume that a single magnetic coil may be part of the first set of coils 155 (stimulating the auditory nerve such that the user can interpret sound within their environment) 25% of the time. If, through the disclosed in-situ stimulation adjustment process 200, it is determined that this single magnetic coil may be turned off because it does not provide a benefit to the user, the following power savings may be realized:

If constantly powered on: 250 mW=250 millijoules (mJ)/ second (s)=900 joules (J)/hour (hr)

Part of the first set of coils 155 25% of the time: 900*0.25=225 J/hr=5400 J/day=37800 J/week=1,965, 600 J/year A typical cochlear implant battery operates at 1.2 volts (V)

1,965,600/1.2 V=1,638,000 Coulombs=455 ampere hour (Ah)→savings if we do not power on a single magnetic coil per year Turning off a single coil for 1 year saves the equivalent capacity of ~9 car batteries According to at least one embodiment, the in-situ adjustments made to the stimulation of the first set of coils 155 and consequently the in-situ adjustments made to the stimulator profile 135 may be made, by the ISA module 130A, 130B, 130C in real-time or periodically according to a pre-defined schedule (e.g., once per day, once per week, bi-weekly, monthly, etc.).

According to at least one further embodiment, ISA module 130A, 130B, 130C may display the user's stimulation profile 135 via a computing device of the user (e.g., client computing device 102) or via a computing device of a medical provider of the user (e.g., server 112), or both. In doing so, in-situ adjustments made to the stimulator profile 135 may be reviewed by the user and/or the medical provider. Moreover, in-situ adjustments of the stimulator profile 135 may be made by an ISA module 130A, 130B, 130C located on another computing device, such as the client computing device 102 or the server 112, in communication with the external device 110 via the network 114.

It may be appreciated that FIG. 2 provides only an illustration of one implementation and does not imply any limitations with regard to how different embodiments may be implemented. Many modifications to the depicted environments may be made based on design and implementation requirements.

Figure 3:
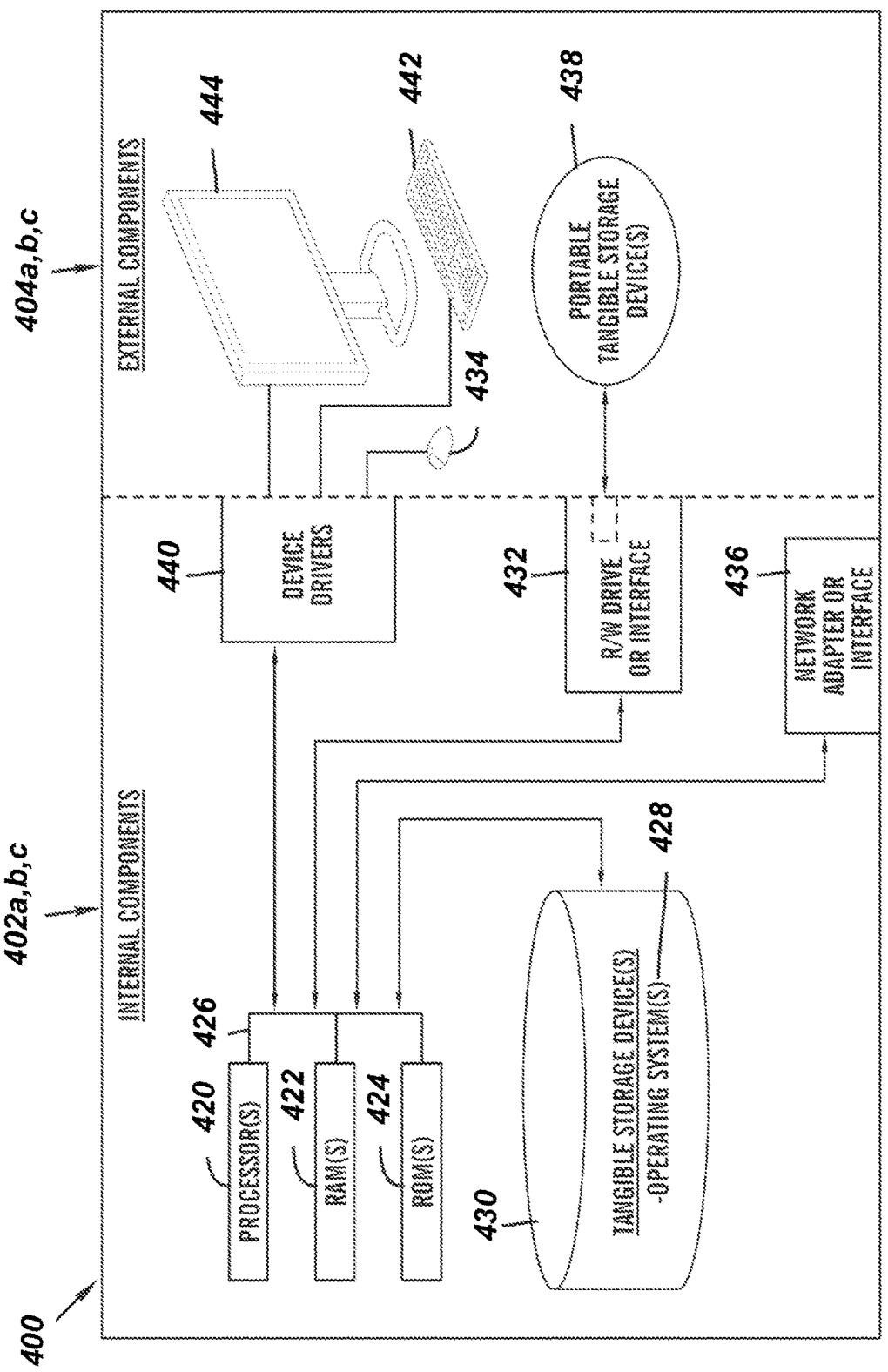
FIG. 3 is a functional block diagram of internal and external components of computers and servers depicted in FIG. 1 according to at least one embodiment.

FIG. 3 is a block diagram 400 of internal and external components of the client computing device 102, the external device 110, and the server 112 depicted in FIG. 1 in accordance with an embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

The data processing system 402, 404 is representative of any electronic device capable of executing machine-readable program instructions. The data processing system 402, 404 may be representative of a smart phone, a computer system, PDA, or other electronic devices. Examples of computing systems, environments, and/or configurations that may represented by the data processing system 402, 404 include, but are not limited to, personal computer systems, server computer systems, thin clients, thick clients, handheld or laptop devices, multiprocessor systems, microprocessor-based systems, network PCs, minicomputer systems, IoT devices, edge devices, and distributed cloud computing environments that include any of the above systems or devices.

The external device 110, the client computing device 102, and the server 112 may include respective sets of internal components 402a,b,c and external components 404a,b,c illustrated in FIG. 3. Each of the sets of internal components 402 include one or more processors 420, one or more computer-readable RAMs 422, and one or more computer-readable ROMs 424 on one or more buses 426, and one or more operating systems 428 and one or more computer-readable tangible storage devices 430. The one or more operating systems 428, the software program 108 and the ISA module 130B in the client computing device 102, the ISA module 130C in the server 112, and the ISA module 130A in the external device 110 are stored on one or more of the respective computer-readable tangible storage devices 430 for execution by one or more of the respective processors 420 via one or more of the respective RAMs 422 (which typically include cache memory). In the embodiment illustrated in FIG. 3, each of the computer-readable tangible storage devices 430 is a magnetic disk storage device of an internal hard drive. Alternatively, each of the computer-readable tangible storage devices 430 is a semiconductor storage device such as ROM 424, EPROM, flash memory or any other computer-readable tangible storage device that can store a computer program and digital information.

Each set of internal components 402a,b,c also includes a RAY drive or interface 432 to read from and write to one or more portable computer-readable tangible storage devices 438 such as a CD-ROM, DVD, memory stick, magnetic tape, magnetic disk, optical disk or semiconductor storage device. A software program, such as the ISA module 130A, 130B, 130C can be stored on one or more of the respective portable computer-readable tangible storage devices 438, read via the respective RAY drive or interface 432, and loaded into the respective hard drive 430.

Each set of internal components 402*a,b,c* also includes network adapters or interfaces 436 such as a TCP/IP adapter cards, wireless Wi-Fi interface cards, wireless Bluetooth® interface cards, or 3G or 4G wireless interface cards or other wired or wireless communication links. The software program 108 and the ISA module 130B in the client computing device 102, the ISA module 130C in the server 112, and the ISA module 130A in the external device 110 can be downloaded to the client computing device 102, the server 112, and the external device 110 from an external computer via a network (for example, the Internet, a local area network or other, wide area network) and respective network adapters or interfaces 436. From the network adapters or interfaces 436, the software program 108 and the ISA module 130B in the client computing device 102, the ISA module 130C in the server 112, and the ISA module 130A in the external device 110 are loaded into the respective hard drive 430. The network may comprise copper wires, optical fibers, wireless transmission, routers, firewalls, switches, gateway computers and/or edge servers.

Each of the sets of external components 404*a,b,c* can include a computer display monitor 444, a keyboard 442, and a computer mouse 434. External components 404*a,b,c* can also include touch screens, virtual keyboards, touch pads, pointing devices, and other human interface devices. Each of the sets of internal components 402*a,b,c* also includes device drivers 440 to interface to computer display monitor 444, keyboard 442, and computer mouse 434. The device drivers 440, R/W drive or interface 432, and network adapter or interface 436 comprise hardware and software (stored in storage device 430 and/or ROM 424).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
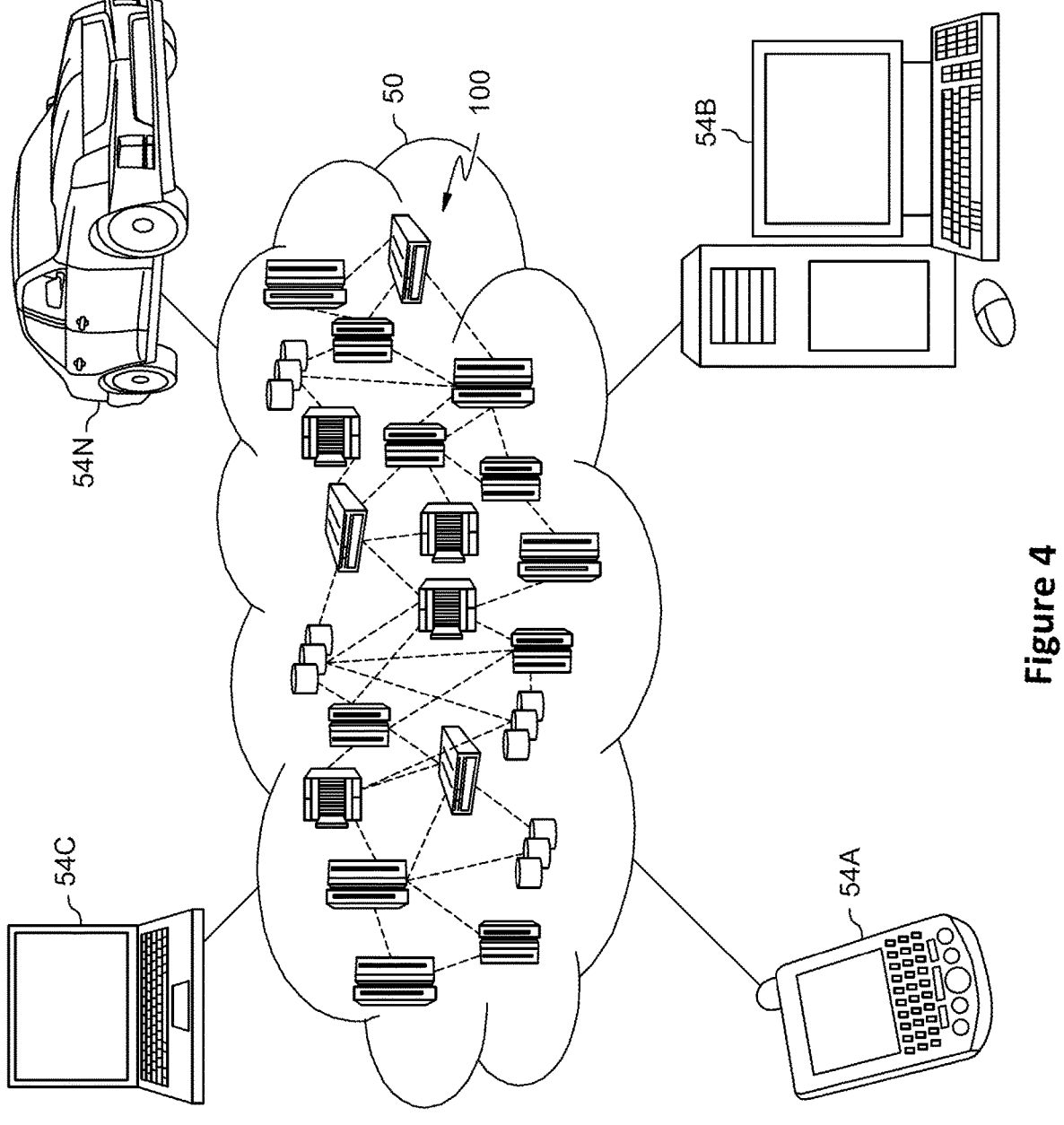
FIG. 4 depicts a cloud computing environment according to an embodiment of the present invention.

Referring now to FIG. 4, illustrative cloud computing environment 50 is depicted. As shown, cloud computing environment 50 comprises one or more cloud computing nodes 100 with which local computing devices used by cloud consumers, such as, for example, personal digital assistant (PDA) or cellular telephone 54A, desktop computer 54B, laptop computer 54C, and/or automobile computer system 54N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 100 and cloud computing environment 50 can communicate with any type of computerized device over any type of network and/or network addressable connection (e.g., using a web browser).

Figure 5:
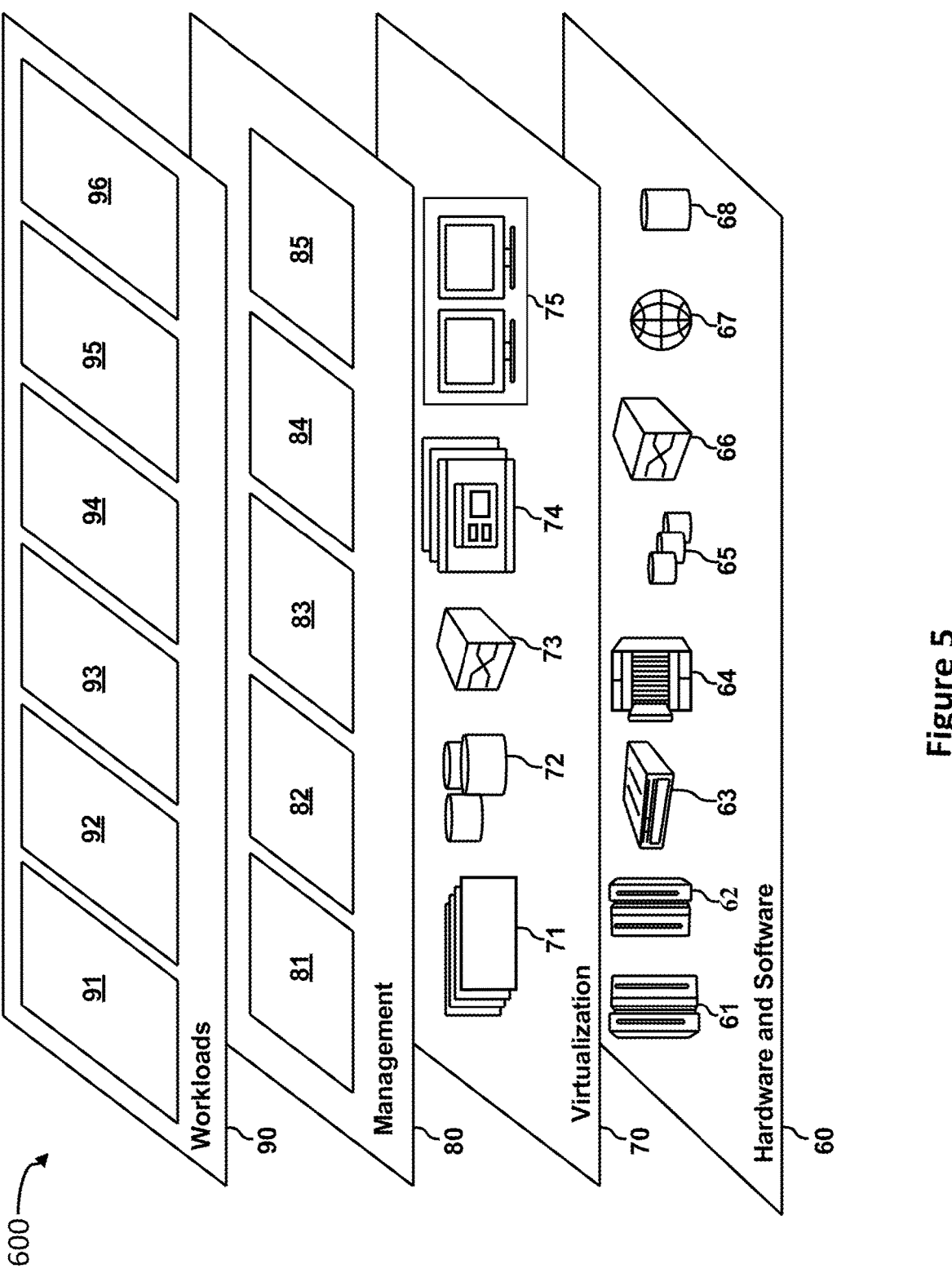
FIG. 5 depicts abstraction model layers according to an embodiment of the present invention.

Referring now to FIG. 5, a set of functional abstraction layers 600 provided by cloud computing environment 50 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and in-situ adjustment 96.

In-situ adjustment 96 may relate to performing in-situ stimulation adjustments of a cochlear implant having magnetic electrodes.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, the method comprising:

identifying a first set of magnetic coils and a second set of magnetic coils based on dominant frequency components of a received sound, wherein the first set and the second set are located on an electrode array of a cochlear implant (CI), and wherein the electrode array is implanted within a cochlea of a user having the CI;

activating, according to a stimulator profile of the user, the first set via an electric current sent to the first set in order to stimulate cochlear neurons;

recording, via the second set, a cochlear neuronal response to the activation of the first set;

determining that an in-situ adjustment to the activation of the first set is required based on analysis of the cochlear neuronal response recorded via the second set;

adjusting the electric current sent to the first set based on the analysis; and adjusting the stimulator profile to reflect adjustments to the electric current sent to the first set.

2. The method of claim 1, wherein the cochlear neuronal response comprises an electric current measurement that is induced onto one or more magnetic coils of the second set by action potentials of cochlear neurons stimulated by the first set of magnetic coils.

3. The method of claim 1, wherein adjusting the stimulator profile further comprises:

determining that the cochlear neuronal response is below a threshold value;

determining that the electric current sent to one or more magnetic coils of the first set is below a maximum permittable value; and increasing the electric current sent to one or more magnetic coils of the first set.

4. The method of claim 1, wherein adjusting the stimulator profile further comprises:

determining that the electric current sent to one or more magnetic coils of the first set is equal to a maximum permittable value;

determining that the cochlear neuronal response is below a threshold value; and permanently assigning the one or more magnetic coils to the second set.

5. The method of claim 1, wherein identification of the first set of magnetic coils is based on placements of magnetic coils within the cochlea being in proximity to frequency input regions of the cochlea which correlate to the dominant frequency components of the received sound, and wherein any magnetic coil not identified as part of the first set is identified as part of the second set.

6. The method of claim 1, wherein the stimulator profile comprises a database storing a tonotopic mapping of the cochlea of the user which correlates different frequency input regions of the cochlea with identified magnetic coils, and wherein the stimulator profile specifies which identified magnetic coils to identify as being within the first set based on the dominant frequency components of the received sound, and wherein the stimulator profile also stores a specified electric current coil activation value for each identified magnetic coil, a volume vs. current graph for specified frequencies, or a multiplication factor for specified frequencies.

7. The method of claim 1, wherein adjusting the stimulator profile occurs in real-time or periodically.

8. A computer system, the computer system comprising:

one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:

identifying a first set of magnetic coils and a second set of magnetic coils based on dominant frequency components of a received sound, wherein the first set and the second set are located on an electrode array of a cochlear implant (CI), and wherein the electrode array is implanted within a cochlea of a user having the CI;

activating, according to a stimulator profile of the user, the first set via an electric current sent to the first set in order to stimulate cochlear neurons;

recording, via the second set, a cochlear neuronal response to the activation of the first set;

determining that an in-situ adjustment to the activation of the first set is required based on analysis of the cochlear neuronal response recorded via the second set;

adjusting the electric current sent to the first set based on the analysis; and adjusting the stimulator profile to reflect adjustments to the electric current sent to the first set.

9. The computer system of claim 8, wherein the cochlear neuronal response comprises an electric current measurement that is induced onto one or more magnetic coils of the second set by action potentials of cochlear neurons stimulated by the first set of magnetic coils.

10. The computer system of claim 8, wherein adjusting the stimulator profile further comprises:

determining that the cochlear neuronal response is below a threshold value;

determining that the electric current sent to one or more magnetic coils of the first set is below a maximum permittable value; and increasing the electric current sent to one or more magnetic coils of the first set.

11. The computer system of claim 8, wherein adjusting the stimulator profile further comprises:

determining that the electric current sent to one or more magnetic coils of the first set is equal to a maximum permittable value;

determining that the cochlear neuronal response is below a threshold value; and permanently assigning the one or more magnetic coils to the second set.

12. The computer system of claim 8, wherein identification of the first set of magnetic coils is based on placements of magnetic coils within the cochlea being in proximity to frequency input regions of the cochlea which correlate to the dominant frequency components of the received sound, and wherein any magnetic coil not identified as part of the first set is identified as part of the second set.

13. The computer system of claim 8, wherein the stimulator profile comprises a database storing a tonotopic mapping of the cochlea of the user which correlates different frequency input regions of the cochlea with identified magnetic coils, and wherein the stimulator profile specifies which identified magnetic coils to identify as being within the first set based on the dominant frequency components of the received sound, and wherein the stimulator profile also stores a specified electric current coil activation value for each identified magnetic coil, a volume vs. current graph for specified frequencies, or a multiplication factor for specified frequencies.

14. The computer system of claim 8, wherein adjusting the stimulator profile occurs in real-time or periodically.

15. A computer program product, the computer program product comprising:

one or more computer-readable tangible storage medium and program instructions stored on at least one of the one or more tangible storage medium, the program instructions executable by a processor capable of performing a method, the method comprising:

identifying a first set of magnetic coils and a second set of magnetic coils based on dominant frequency components of a received sound, wherein the first set and the second set are located on an electrode array of a cochlear implant (CI), and wherein the electrode array is implanted within a cochlea of a user having the CI;

activating, according to a stimulator profile of the user, the first set via an electric current sent to the first set in order to stimulate cochlear neurons;

recording, via the second set, a cochlear neuronal response to the activation of the first set;

determining that an in-situ adjustment to the activation of the first set is required based on analysis of the cochlear neuronal response recorded via the second set;

adjusting the electric current sent to the first set based on the analysis; and adjusting the stimulator profile.

16. The computer program product of claim 15, wherein the cochlear neuronal response comprises an electric current measurement that is induced onto one or more magnetic coils of the second set by action potentials of cochlear neurons stimulated by the first set of magnetic coils.

17. The computer program product of claim 15, wherein adjusting the stimulator profile further comprises:

determining that the cochlear neuronal response is below a threshold value;

determining that the electric current sent to one or more magnetic coils of the first set is below a maximum permittable value; and increasing the electric current sent to one or more magnetic coils of the first set.

18. The computer program product of claim 15, wherein adjusting the stimulator profile further comprises:

determining that the electric current sent to one or more magnetic coils of the first set is equal to a maximum permittable value;

determining that the cochlear neuronal response is below a threshold value; and permanently assigning the one or more magnetic coils to the second set.

19. The computer program product of claim 15, wherein identification of the first set of magnetic coils is based on placements of magnetic coils within the cochlea being in proximity to frequency input regions of the cochlea which correlate to the dominant frequency components of the received sound, and wherein any magnetic coil not identified as part of the first set is identified as part of the second set.

20. The computer program product of claim 15, wherein the stimulator profile comprises a database storing a tonotopic mapping of the cochlea of the user which correlates different frequency input regions of the cochlea with identified magnetic coils, and wherein the stimulator profile specifies which identified magnetic coils to identify as being within the first set based on the dominant frequency components of the received sound, and wherein the stimulator profile also stores a specified electric current coil activation value for each identified magnetic coil, a volume vs. current graph for specified frequencies, or a multiplication factor for specified frequencies.

* * * * *